United States Patent
Umemura

(10) Patent No.: US 6,677,583 B2
(45) Date of Patent: Jan. 13, 2004

(54) LIQUID CHROMATOGRAPH/MASS SPECTROMETER

(75) Inventor: Yoshikatsu Umemura, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 69 days.

(21) Appl. No.: 10/013,707

(22) Filed: Dec. 13, 2001

(65) Prior Publication Data
US 2002/0074490 A1 Jun. 20, 2002

(30) Foreign Application Priority Data
Dec. 19, 2000 (JP) ........................ 2000-385160

(51) Int. Cl.⁷ .................... B01D 59/44; H01J 49/00
(52) U.S. Cl. .................. 250/288; 250/281; 250/282
(58) Field of Search ................... 250/281–300

(56) References Cited

U.S. PATENT DOCUMENTS 5,789,746 A * 8/1998 Kato et al. .............. 250/288
6,309,541 B1 * 10/2001 Maiefski et al. ......... 210/198.2
6,469,297 B1 * 10/2002 Kato ...................... 250/288

* cited by examiner

Primary Examiner—Bruce Anderson
Assistant Examiner—Erin-Michael Gill
(74) Attorney, Agent, or Firm—Westerman, Hattori, Daniels & Adrian, LLP

(57) ABSTRACT

The present invention proposes a liquid chromatograph/mass spectrometer (LC/MS) constructed so that only necessary data are efficiently collected, and that the apparent dynamic range and/or the operational condition of the MS part is appropriately changed according to the concentrations and/or the qualitative information of the sample components coming from the LC part. In the LC/MS, the passage of the carrier liquid is designed so that the carrier liquid containing the sample is first introduced to an auxiliary detector and then to a main detector (mass spectrometer) with a delay of a preset time period. During the analysis, a controller constructs a chromatogram from the output signal of the auxiliary detector and analyzes its waveform to determine in real-time a time period ts0–te0 corresponding to each peak in the chromatogram. Then, the controller collects the measurement data by the main detector only within a time period ts1–te1 which has a delay of the preset time period Δt from the above time period ts0–te0.

6 Claims, 3 Drawing Sheets

COND. SET (1): SETTINGS BASED ON A METHOD PREPARED BY USER
COND. SET (2): SETTINGS BASED ON MEASUREMENT DATA OF AUX DETECTOR (AUTOMATIC)

LIQUID CHROMATOGRAPH/MASS SPECTROMETER

The present invention relates to a liquid chromatograph/mass spectrometer (LC/MS), and particularly to an automatic control of an LC/MS.

BACKGROUND OF THE INVENTION

An analysis using an LC/MS is performed under certain measurement conditions, which, for example, include the condition of supplying the carrier liquid in the liquid chromatograph part (LC part); the condition for starting/ending the measurement in the mass spectrometer part (MS part); the range of mass numbers to be measured; the measurement mode (selected, for example, from MS mode, MS/MS mode and $MS^n$ mode). These measurement conditions are often changed from time to time in an analysis. For this type of analysis, the user prepares beforehand a "method", which is a time schedule for changing the measurement conditions, while taking into consideration the content of the analysis. The method is stored beforehand in the controller. In a measurement, the controller controls every part of the LC/MS according to the method.

In an analysis using the LC/MS, when the component to be analyzed is known or specified, the time point at which the peak of the objective component appears in the chromatogram (i.e. retention time) can be calculated if the condition of supplying the carrier liquid in the LC part is determined, and also the time point at which the objective component enters the MS part can be calculated. In this case, unnecessary data collection can be avoided if the MS part collects the data only within a certain time period in which the peak passes the MS part. When, on the other hand, the component to be analyzed is unknown (e.g. when impurities are to be detected), it is impossible to know beforehand the time point at which the peak appears. In such a case, one possible measure is to collect all the measurement data over a broad range of mass numbers taking a long period of time and to store the data in a storage device (e.g. hard disk drive). This, however, wastes a large amount of storage space because the information thus collected contains a lot of unnecessary data corresponding to the non-peak sections of the chromatogram (FIG. 5).

A chromatograph/mass spectrometer constructed in view of the above problem is disclosed in the Japanese Examined Patent Publication No. H5-24458 (matured to Japanese Patent No. 1816212). In this chromatograph/mass spectrometer, data of the total ion chromatogram (TIC) collected by a measurement are temporarily stored in an auxiliary memory such as a semiconductor memory. The time range corresponding to the peak or peaks of the chromatogram is identified by analyzing the above data, and only those measurement data within the identified time range are stored in the storage device. For this construction, however, an auxiliary memory operating at a high-speed and having a large capacity is necessary to temporarily store a large amount of data of the total ion chromatogram. Particularly, when the MS part is a time-of-flight (TOF) type, the size of data collected in a mass-scanning operation reaches several hundreds of kilobytes to several megabytes. Furthermore, it is necessary to repeat the mass-scanning from several to more than ten times to adequately analyze the waveform of a chromatogram. To store such a large amount of data, it is necessary to use an expensive semiconductor memory with a large capacity, which increases the production cost.

When the MS part is an ion trap type, the following problem must be considered. In the ion trap mass spectrometer, the trapping space within the electrodes has a limited capacity of ions at a time because of the space charges due to the trapped ions. Therefore, the range (or dynamic range) in which the concentration of the component can be linearly measured is limited to a certain extent. In a conventional improvement, the time period of introducing ions into the ion trap is appropriately restricted according to the concentration of the sample coming from the LC part to increase the apparent dynamic range (i.e. to raise the upper limit). An example of the known methods of automatically carrying out the above operation is Automatic Sensitivity Control (ASC). By this method, the change in the sample concentration is monitored based on the data collected in the previous mass-scanning operation. When the sample concentration is high, the time period of introducing ions into the ion trap is temporarily shortened, as shown in FIG. 6, to prevent the trapping space from being overfilled with the space charges. By this method, however, when a sudden rise of the peak occurs in the chromatogram, the feedback process cannot keep up with the rise in time, which causes a delay of control and yields a distorted chromatogram, as shown in FIG. 7.

When the A/D converter at the output of the ion detector of the MS part has a poor resolving power (or small quantifying bit number), the dynamic range is accordingly narrow. In such a case, it is possible to increase the apparent dynamic range by appropriately switching the gain of the analog amplifier according to the strength of the signal of the ion detector, i.e. by lowering the gain when the strength of the signal is great. In the TOF type of MS, however, it is necessary to A/D-convert the signal at a speed as high as about 500 MHz to several GHz. At such a high speed, the switching speed of the gain of the analog amplifier is slower than the A/D conversion speed, so that a delay of control appears as shown in FIG. 7 in a real-time measurement.

The present invention proposes an LC/MS constructed so that only necessary data are collected efficiently and that the apparent dynamic range of the MS part can be appropriately changed according to the concentrations of the sample components coming from the LC part.

SUMMARY OF THE INVENTION

A liquid chromatograph/mass spectrometer according to the present invention includes:
  a mass spectrometer provided as a main detector;
  an auxiliary detector provided apart from the mass spectrometer;
  a passage for introducing a sample from the liquid chromatograph part first to the auxiliary detector and then to the mass spectrometer part with a delay of a preset time period;
  a peak detector for analyzing a chromatogram constructed from an output signal of the auxiliary detector to determine a retention time of each peak in the chromatogram; and
  a controller for controlling a measurement operation of the mass spectrometer according to the retention time of the peak or peaks in the chromatogram.

The features of the present invention will be clearly understood from the detailed description of a preferred embodiment with reference to the attached drawings.

DETAILED DESCRIPTION OF A PREFERRED EMBODIMENT

Figure 1:
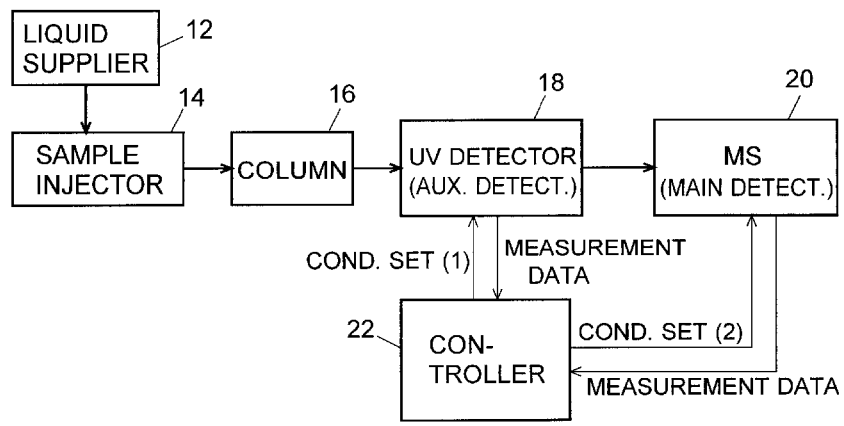
FIG. 1 is a block diagram of the schematic construction of an LC/MS embodying the present invention.

FIG. 1 shows an LC/MS 10 including a liquid supplier 12 for supplying a carrier liquid to a passage, a sample injector 14 for injecting a sample into the carrier liquid flowing in the passage, a column 16 for separating the sample in the carrier liquid into components, two detectors 18, 20, both for producing a signal whose strength corresponds to the concentration of the component of the sample in the carrier liquid, and a controller 22 for controlling the detectors 18, 20.

Of the two detectors, the first detector 18 corresponds to the auxiliary detector of the present invention, and the second detector 20 corresponds to the main detector (mass spectrometer). In FIG. 1, an ultraviolet radiation detector (IV detector) is used as the auxiliary detector 18. Other types of non-destructive detectors, such as a photodiode array (PDA) detector, may also be preferably used. Use of a non-destructive detector as the auxiliary detector, however, is not essential to the present invention. For example, the LC/MS 10 may be changed so that the liquid coming from the column 16 is split into two branches with a splitter; the auxiliary detector 18 is disposed in the first branch; and the main detector 20 is disposed in the second branch. Such a construction allows a destructive detector to be used as the auxiliary detector 18 without causing any problem in the measurement of the sample by the main detector 20. In should be noted that, when the passage is constructed as described above, the length and volume of the branches should be appropriately designed so that the time required for the carrier liquid to flow from the splitter to the auxiliary detector 18 is adequately shorter than that required for the liquid to flow from the splitter to the main detector 20.

With the LC/MS 10 of FIG. 1, an analysis is carried out as follows. First, according to the purpose of the analysis, the user either creates a new method or selects one of the methods prepared beforehand, and commands the controller 22 to start the analysis. Here, it is assumed that all the components contained in the sample are to be analyzed, without specifying any component as the objective component. On receiving the command, the controller 22 sets the measurement parameters according to the method, where the parameters include the flow rate of the carrier liquid supplied by the liquid supplier 12, the temperature of the column 16, etc. After a lapse of an adequate time period, the sample injector 14 injects a sample into the carrier liquid. In the column 16, the sample introduced into the carrier liquid is separated into components, which enter the UV detector 18. The UV detector 18 detects each component and produces a signal corresponding to the concentration of the component.

Figure 2:
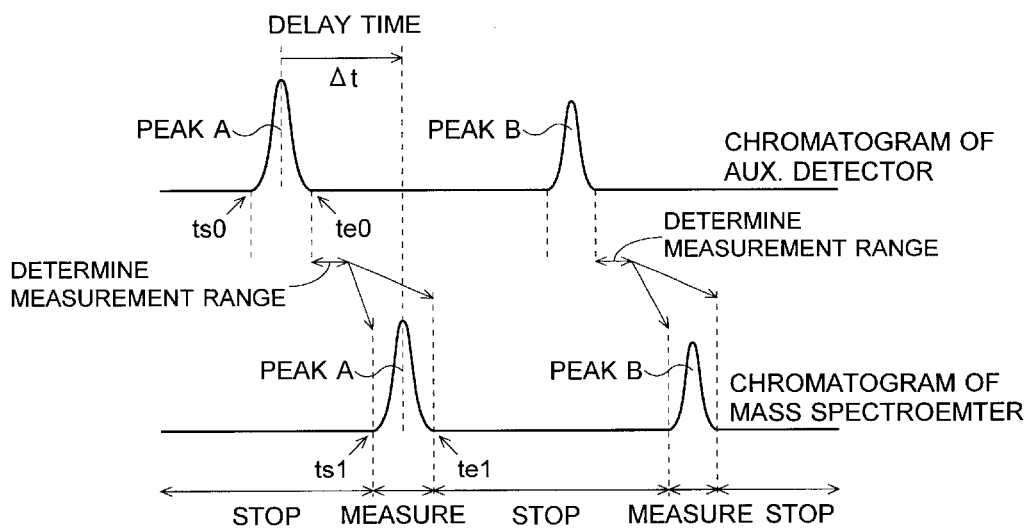
FIG. 2 shows an example of the method of controlling the operation of the mass spectrometer based on the measurement data taken by the auxiliary detector.

The controller 22 constructs a chromatogram in real-time by processing the measurement data obtained from the output signal of the UV detector 18 as described above, and analyzes the waveform of the chromatogram to detect a peak or peaks. Referring to FIG. 2, the waveform analysis relating to the peak A in the chromatogram is performed as follows. First, the controller 22 stores the beginning time point ts0 and the ending time point te0 of the peak A in the memory (not shown). After the whole peak A has passed, the controller 22 determines the time period ts1–te1 which has a delay of a preset time period $\Delta t$ from the time period ts0–te0 as the measurement range for the main detector 20. The time period $\Delta t$ is calculated beforehand based on the flow rate of the carrier liquid, the length and volume of the passage from the UV detector 18 to the mass spectrometer 20, etc. Though the determination of the measurement range is completed in a very short time, the passage is designed so that the time period $\Delta t$ is adequately long lest the component of the peak A should reach the mass spectrometer 20 before the determination of the measurement range.

After determining the measurement range as described above, the controller 22 starts the measurement with the mass spectrometer 20 at the time point ts1. That is, the controller 22 starts collecting measurement data converted from the output signal of the mass spectrometer 20 and stops collecting the data at the time point te1. By such a method, all the data corresponding to the peak A are collected without omission, whereas unnecessary data are not collected. Thus, the storage space of the storage device (not shown) is used efficiently.

Figure 3:
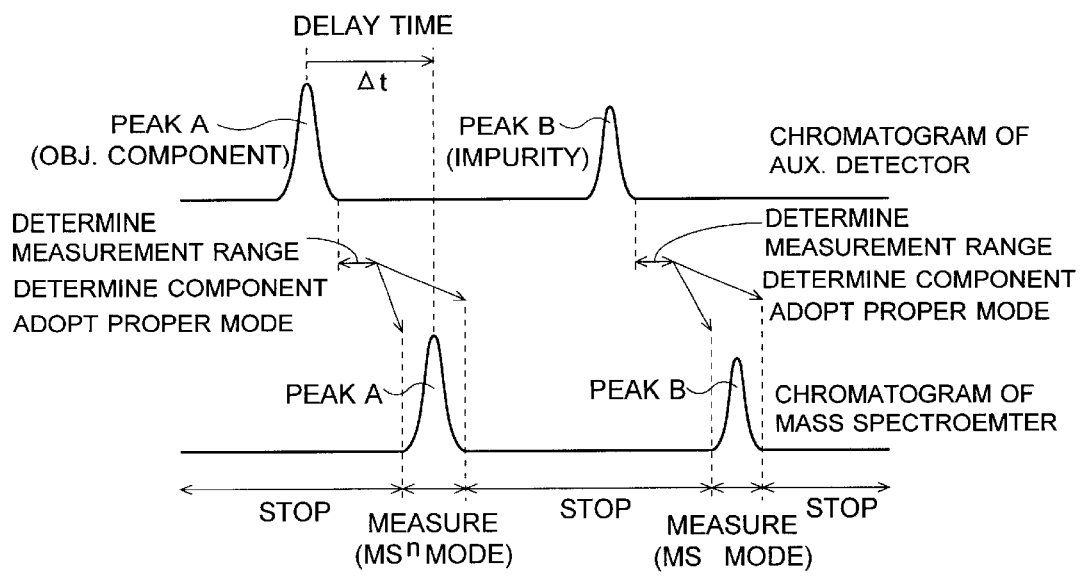
FIG. 3 shows an example of the method of adopting different measurement modes for the objective component to be analyzed and other components.

In the analysis using the LC/MS 10 of FIG. 1, the controller 22 can distinguish the peak of the objective component from the peaks of the other components or impurities by appropriately selecting the measurement wavelength of the UV detector 18 according to the objective components. Otherwise, the PDA detector or other types of detectors capable of qualitative detection may be used as the auxiliary detector 18 to distinguish the components. In the case of distinguishing the component, the controller 22 may be constructed so that the objective component is measured in a predetermined measurement mode (e.g. $MS^n$ mode) while the other components (or impurities) are measured in a different mode (e.g. MS mode). That is, as shown in FIG. 3, on every detection of the peak, the controller 22 not only determines the time range for the mass spectrometer 20 to measure the peak, as described above, but also determines whether the component of the peak is the objective component, and adopts the proper measurement mode according to the determination result. This control method enables the real-time switching of the measurement mode according to the component detected in the measurement. Thus, it is no longer necessary to separately carry out the measurement of the objective component and the measurement of the impurities, so that the efficiency of analysis is improved.

Figure 4:
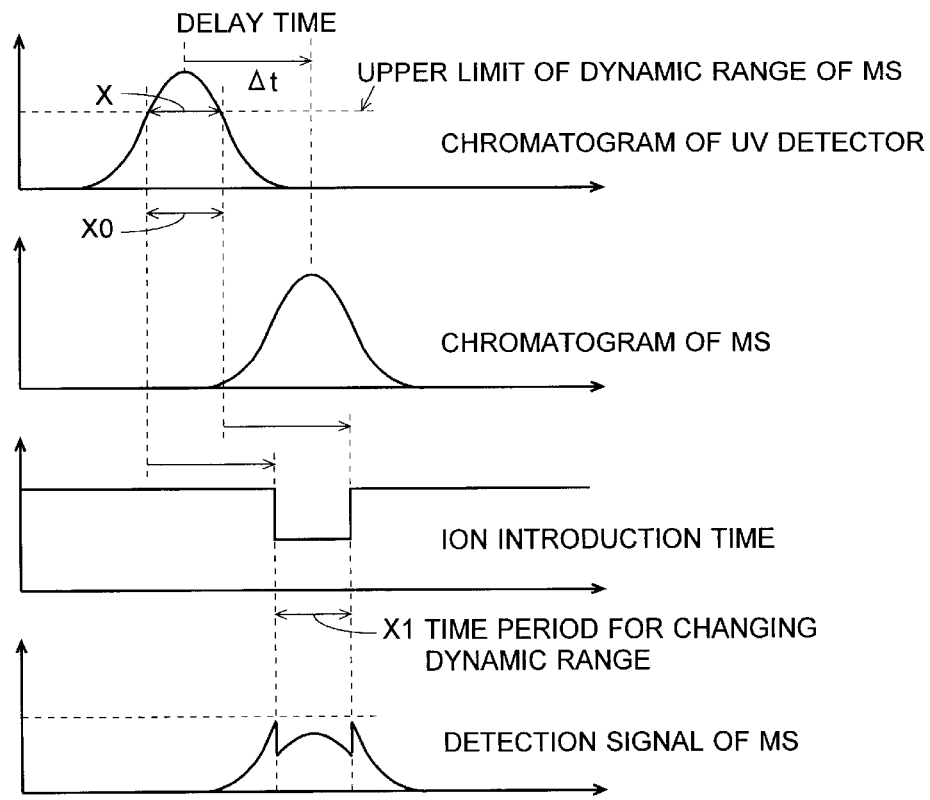
FIG. 4 shows an example of the method of increasing the apparent dynamic range of the mass spectrometer according to the concentration of the component.
Figure 5:
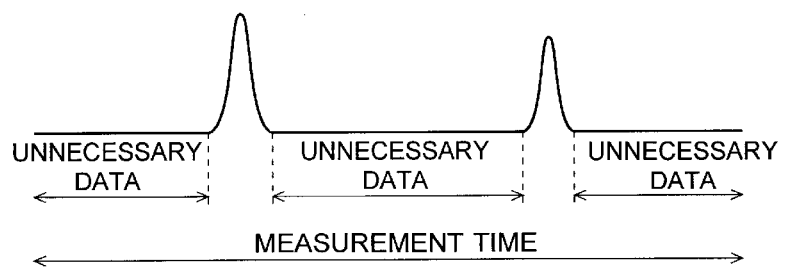
FIG. 5 shows the time periods in which unnecessary data appear in a chromatogram.
Figure 6:
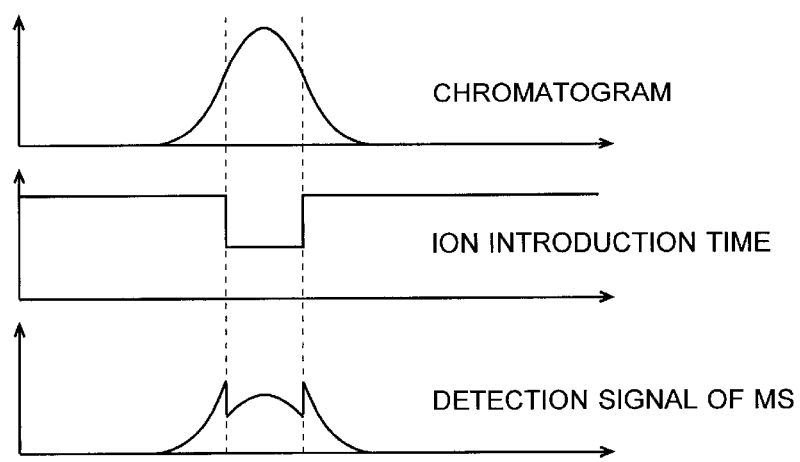
FIG. 6 shows an example of the method of changing the apparent dynamic range of the mass spectrometer according to the concentration of the component.
Figure 7:
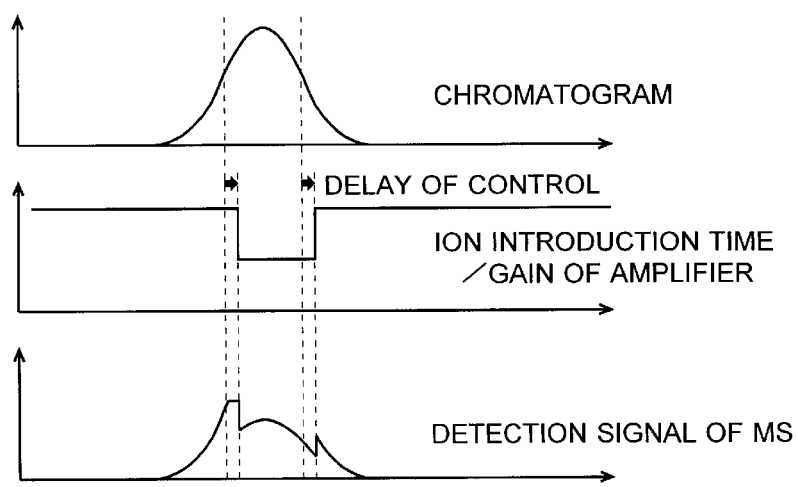
FIG. 7 shows how a delay occurs in the process of changing the dynamic range in the control shown in FIG. 6.

Regarding the analysis with the LC/MS of FIG. 1, a method of increasing the apparent dynamic range of the mass spectrometer according to the concentration of the component is described referring to FIG. 4. It is assumed hereby that the mass spectrometer 20 is an ion trap type.

In the waveform analysis based on the measurement data converted from the output signal of the auxiliary detector 18, the controller 22 not only identifies the beginning time point and the ending time point of each peak, as described above, but also determines the strength of the signal at every time point while the peak is being detected. When, as denoted by X, there is a time period in which the strength of the signal exceeds the strength corresponding to the upper limit of the dynamic range of the mass spectrometer 20, the controller 22 determines a time period X0 of the same length as the time period X or slightly longer than that, and determines a time period X1 for changing the dynamic range which has a delay of the preset time period Δt from the time period X0. After that, the controller 22 shortens the time period of introducing ions into the ion trap throughout the time period X1. As a result, an ideal waveform free from saturated part is obtained, as shown in the lowest part of FIG. 4.

In the example of FIG. 4, the dynamic range is selected from the two levels, and the time period of introducing ions is set to the lower (half) level within the time period X1. It should be noted that the method of changing the dynamic range is not restricted to the above. For example, according to the waveform of the chromatogram taken by the auxiliary detector 18, the dynamic range may be continuously changed to produce an approximately flat chromatogram from the output signal of the mass spectrometer 20.

When the auxiliary detector 18 produces data of an absorption spectrum rather than a peak spectrum as described above, the controller 22 can perform the above-described processes in the same way.

Thus, in the LC/MS according to the present invention, all the measurement data collected with the mass spectrometer are not stored in the storage device, but only the necessary and sufficient measurement data corresponding to the sample peak are stored in the storage device, so that the storage space of the storage device is used efficiently. Since it is not necessary to temporarily store unnecessary measurement data, it is possible to suppress the production cost by using a relatively inexpensive storage device and/or memory of a small capacity. In the conventional LC/MS, when the retention time of an objective component changes depending on the condition of the column or the carrier liquid, the method must be modified according to the change. With the present invention, on the other hand, such a modification is not necessary, so that the maintainability is improved. Further, the automatic real-time switching of the apparent dynamic range of the mass spectrometer provides a greatly improved performance of the system.

What is claimed is:

1. A liquid chromatograph/mass spectrometer, comprising:
    a mass spectrometer provided as a main detector;
    an auxiliary detector provided apart from the mass spectrometer;
    a passage for introducing a sample from a liquid chromatograph part first to the auxiliary detector and then into the mass spectrometer with a delay of a preset time period;
    a peak detector for analyzing a chromatogram constructed from an output signal of the auxiliary detector and for determining a first time period in which the peak appears in the chromatogram; and
    a controller for controlling a measurement operation of the mass spectrometer in a second time period having a delay of the preset time period from the first time period.

2. The liquid chromatograph/mass spectrometer according to claim 1, wherein the auxiliary detector is a non-destructive type.

3. The liquid chromatograph/mass spectrometer according to claim 1, wherein, on every detection of the peak, the controller determines whether a component of the peak is an objective component and adopts a measurement mode according whether the component of the peak is the objective component.

4. The liquid chromatograph/mass spectrometer according to claim 1, wherein the controller monitors a strength of the output signal of the auxiliary detector and determines a time period to increase an apparent dynamic range of the mass spectrometer when there is a time period in which the strength of the output signal exceeds a strength corresponding to an upper limit of the dynamic range of the mass spectrometer.

5. A liquid chromatograph/mass spectrometer, comprising:
    a mass spectrometer provided as a main detector;
    an auxiliary detector provided apart from the mass spectrometer;
    a passage for introducing a sample from a liquid chromatograph part first to the auxiliary detector and then into the mass spectrometer with a delay of a preset time period;
    a peak detector for analyzing a chromatogram constructed from an output signal of the auxiliary detector to determine a retention time of each peak in the chromatogram; and
    a controller for controlling a measurement operation of the mass spectrometer according to the retention time of the peak or peaks in the chromatogram;
    wherein, on every detection of the peak, the controller determines whether a component of the peak is an objective component and adopts a measurement mode according whether the component of the peak is the objective component.

6. A liquid chromatograph/mass spectrometer, comprising:
    a mass spectrometer provided as a main detector;
    an auxiliary detector provided apart from the mass spectrometer;
    a passage for introducing a sample from a liquid chromatograph part first to the auxiliary detector and then into the mass spectrometer with a delay of a preset time period;
    a peak detector for analyzing a chromatogram constructed from an output signal of the auxiliary detector to determine a retention time of each peak in the chromatogram; and
    a controller for controlling a measurement operation of the mass spectrometer according to the retention time of the peak or peaks in the chromatogram;
    wherein the controller monitors a strength of the output signal of the auxiliary detector and determines a time period to increase an apparent dynamic range of the mass spectrometer when there is a time period in which the strength of the output signal exceeds a strength corresponding to an upper limit of the dynamic range of the mass spectrometer.

* * * * *